US008100959B2

(12) United States Patent
Que et al.

(10) Patent No.: US 8,100,959 B2
(45) Date of Patent: Jan. 24, 2012

(54) LOADING DEVICE FOR A PULMONARY IMPLANT

(75) Inventors: Like Que, Livermore, CA (US); Hoang Nguyen, San Jose, CA (US); Son Gia, San Jose, CA (US); Ajitkumar Nair, Milpitas, CA (US); Roger Farnholtz, Fremont, CA (US); George Surjan, San Jose, CA (US); Andrew Huffmaster, Newark, CA (US); Jeffrey Lee, San Ramon, CA (US)

(73) Assignee: Pulmonx Corporation, Redwood City, CA (US)

( * ) Notice: Subject to any disclaimer, the term of this patent is extended or adjusted under 35 U.S.C. 154(b) by 584 days.

(21) Appl. No.: 12/043,404

(22) Filed: Mar. 6, 2008

(65) Prior Publication Data
US 2008/0221703 A1 Sep. 11, 2008

Related U.S. Application Data

(60) Provisional application No. 60/893,940, filed on Mar. 9, 2007.

(51) Int. Cl.
*A61F 2/06* (2006.01)

(52) U.S. Cl. ............ 623/1.12; 623/1.11; 623/1.23; 606/108

(58) Field of Classification Search ............ 606/108; 623/1.11, 1.12, 1.23, 2.11
See application file for complete search history.

(56) References Cited

U.S. PATENT DOCUMENTS

| 3,322,126 A | 5/1967 | Rusch et al. |
| 3,498,286 A | 3/1970 | Polanyi et al. |
| 3,542,026 A | 11/1970 | Bledsoe |

(Continued)

FOREIGN PATENT DOCUMENTS
WO WO 92/10971 7/1992
(Continued)

OTHER PUBLICATIONS

PCT International Search Report and Written Opinion of PCT Application No. PCT/US08/56289, dated Aug. 26, 2008, 9 pages total.

*Primary Examiner* — Corrine M McDermott
*Assistant Examiner* — Todd J Scherbel
(74) *Attorney, Agent, or Firm* — Wilson Sonsini Goodrich & Rosati

(57) ABSTRACT

Devices for loading a collapsible implant onto a delivery catheter. In one aspect, a loading device comprises an outer tubular structure and an inner tubular structure. The outer tubular structure comprises a narrowing passage configured to receive a catheter at one end and a collapsible implant at another end. The inner tubular structure is configured to move slidably and co-axially within the outer tubular structure. The inner tubular structure comprises a carrier pin configured to move within the narrowing passage as the inner tubular structure slides into the outer tubular structure. The sliding of the inner tubular structure into the outer tubular structure causes an implant mounted on the carrier pin to collapse as the implant moves through the narrowing passage and into the distal end of a catheter. In an optional aspect, the outer tubular structure further comprises a grasper to stabilize the catheter for receipt of the collapsible implant, and the internal diameter of the inner tubular structure varies to cause the grasper to first contract and stabilize the catheter, and then expand and release the catheter, as the grasper moves into the inner tubular structure.

7 Claims, 21 Drawing Sheets

U.S. PATENT DOCUMENTS

| | | | |
|---|---|---|---|
| 3,669,098 A | 6/1972 | Takahashi | |
| 3,677,262 A | 7/1972 | Zukowski | |
| 3,776,222 A | 12/1973 | Smiddy | |
| 3,866,599 A | 2/1975 | Johnson | |
| 3,913,568 A | 10/1975 | Carpenter | |
| 4,041,936 A | 8/1977 | Carden | |
| 4,327,720 A | 5/1982 | Bronson et al. | |
| 4,327,721 A | 5/1982 | Goldin et al. | |
| 4,453,545 A | 6/1984 | Inoue | |
| 4,468,216 A | 8/1984 | Muto | |
| 4,567,882 A | 2/1986 | Heller | |
| 4,716,896 A | 1/1988 | Ackerman | |
| 4,742,819 A | 5/1988 | George | |
| 4,784,133 A | 11/1988 | Mackin | |
| 4,819,664 A | 4/1989 | Nazari | |
| 4,846,153 A | 7/1989 | Berci | |
| 4,850,371 A | 7/1989 | Broadhurst et al. | |
| 4,862,874 A | 9/1989 | Kellner | |
| 4,896,941 A | 1/1990 | Hayashi et al. | |
| 4,949,716 A | 8/1990 | Chenoweth | |
| 4,955,375 A | 9/1990 | Martinez | |
| 4,958,932 A | 9/1990 | Kegelman et al. | |
| 4,961,738 A | 10/1990 | Mackin | |
| 4,976,710 A | 12/1990 | Mackin | |
| 5,056,529 A | 10/1991 | de Groot | |
| 5,143,062 A | 9/1992 | Peckham | |
| 5,146,916 A | 9/1992 | Catalani | |
| 5,285,778 A | 2/1994 | Mackin | |
| 5,309,903 A | 5/1994 | Long | |
| 5,331,947 A | 7/1994 | Shturman | |
| 5,361,753 A | 11/1994 | Pothmann et al. | |
| 5,477,851 A | 12/1995 | Callaghan et al. | |
| 5,499,625 A | 3/1996 | Frass et al. | |
| 5,598,840 A | 2/1997 | Iund et al. | |
| 5,642,730 A | 7/1997 | Baran | |
| 5,645,519 A | 7/1997 | Lee et al. | |
| 5,653,231 A | 8/1997 | Bell | |
| 5,660,175 A | 8/1997 | Dayal | |
| 5,682,880 A | 11/1997 | Brain | |
| 5,707,352 A | 1/1998 | Sekins et al. | |
| 5,725,519 A * | 3/1998 | Penner et al. | 606/1 |
| 5,752,921 A | 5/1998 | Orr | |
| 5,830,222 A | 11/1998 | Makower | |
| 5,840,064 A | 11/1998 | Liprie | |
| 5,957,949 A | 9/1999 | Leonhardt et al. | |
| 5,974,652 A | 11/1999 | Kimes et al. | |
| 5,992,000 A * | 11/1999 | Humphrey et al. | 29/516 |
| 6,068,635 A * | 5/2000 | Gianotti | 29/235 |
| 6,096,027 A * | 8/2000 | Layne | 606/1 |
| 6,132,458 A * | 10/2000 | Staehle et al. | 623/1.11 |
| 6,165,209 A * | 12/2000 | Patterson et al. | 623/1.1 |
| 6,287,290 B1 | 9/2001 | Perkins et al. | |
| 6,398,775 B1 | 6/2002 | Perkins et al. | |
| 6,527,761 B1 | 3/2003 | Buch et al. | |
| 6,585,639 B1 | 7/2003 | Kotmel et al. | |
| 6,709,401 B2 | 3/2004 | Perkins et al. | |
| 7,780,697 B2 * | 8/2010 | Gilson et al. | 606/200 |
| 2003/0083730 A1 * | 5/2003 | Stinson | 623/1.11 |
| 2003/0225445 A1 * | 12/2003 | Derus et al. | 623/1.11 |
| 2005/0203483 A1 | 9/2005 | Perkins et al. | |
| 2006/0162731 A1 * | 7/2006 | Wondka et al. | 128/207.14 |
| 2007/0270937 A1 * | 11/2007 | Leanna | 623/1.12 |

FOREIGN PATENT DOCUMENTS

| | | |
|---|---|---|
| WO | WO 95/33506 | 12/1995 |
| WO | WO 98/48706 | 11/1998 |

* cited by examiner

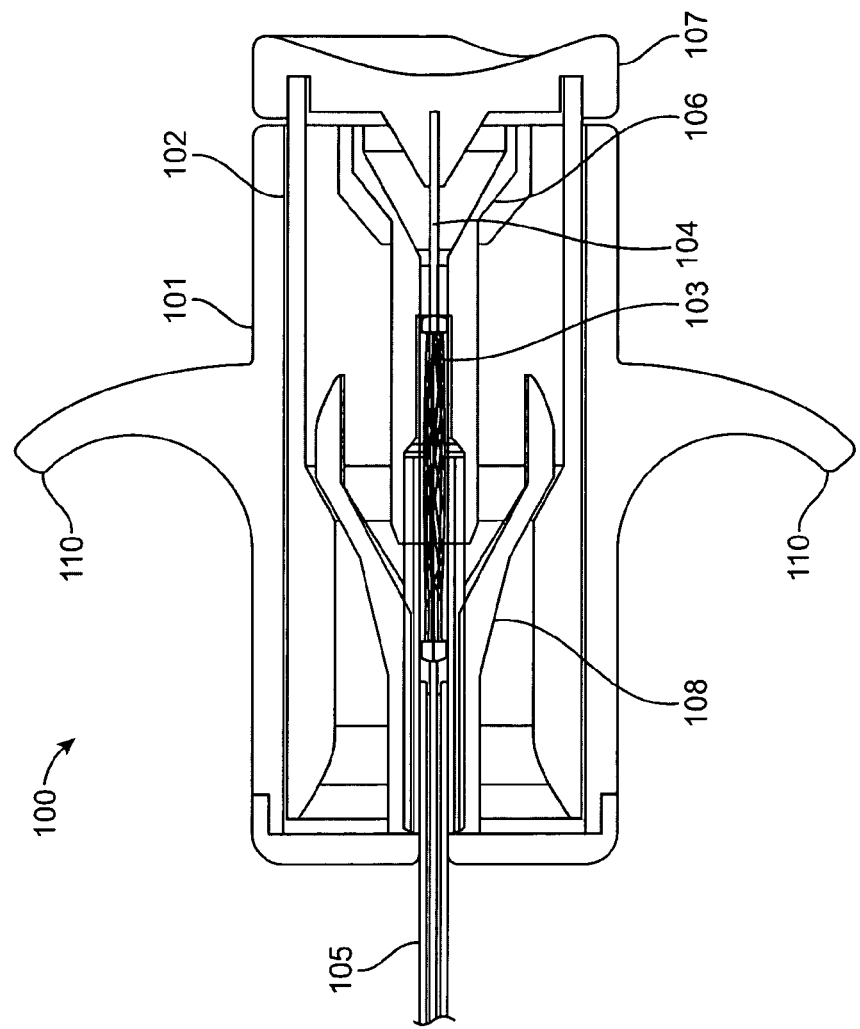

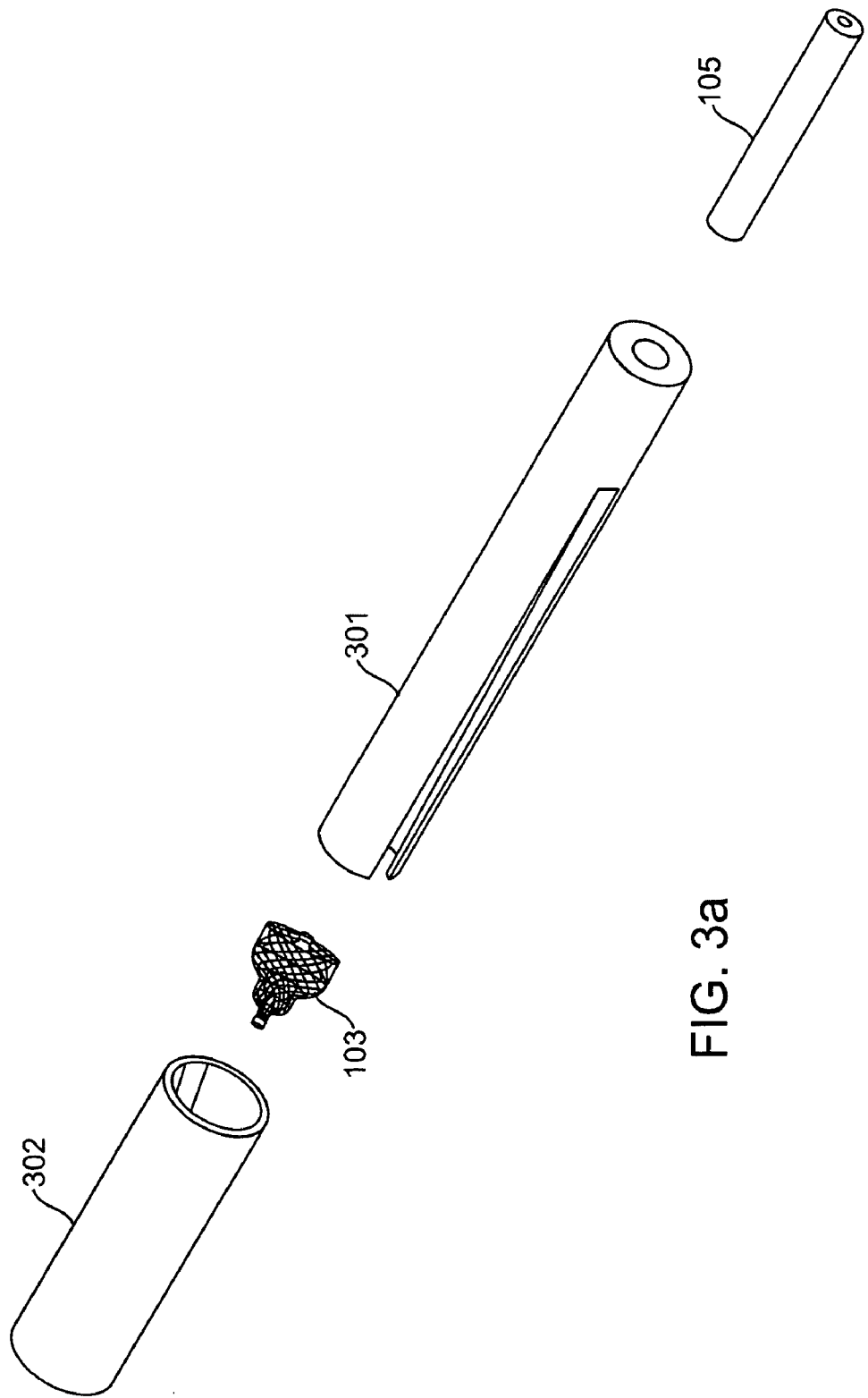

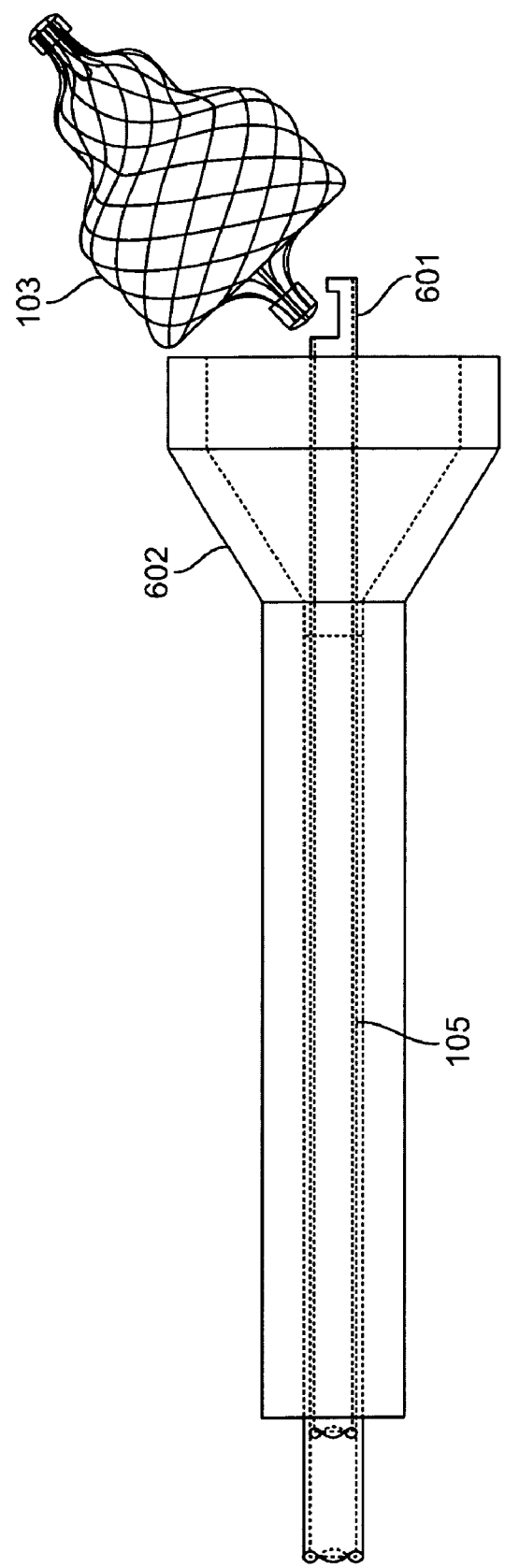

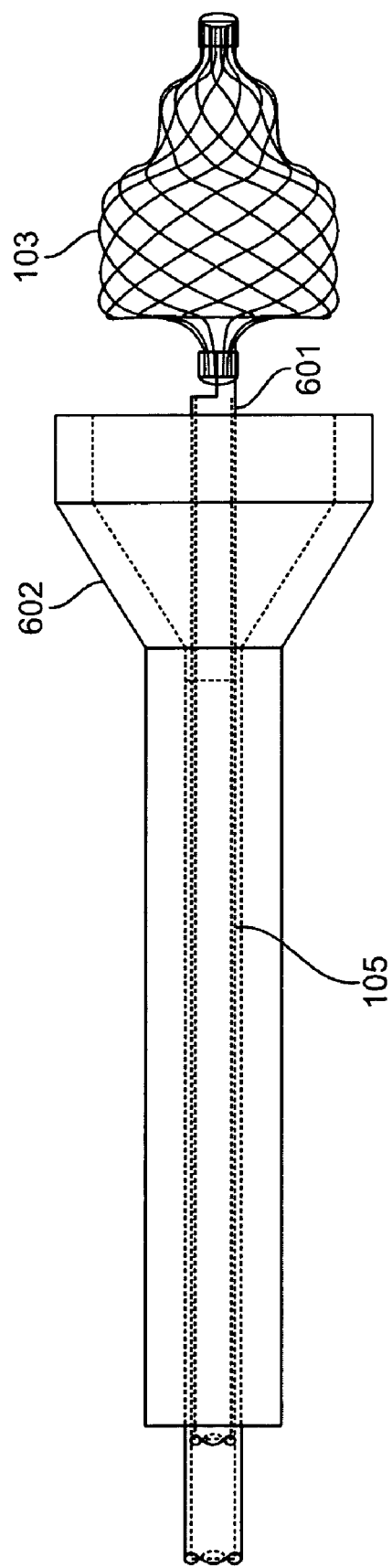

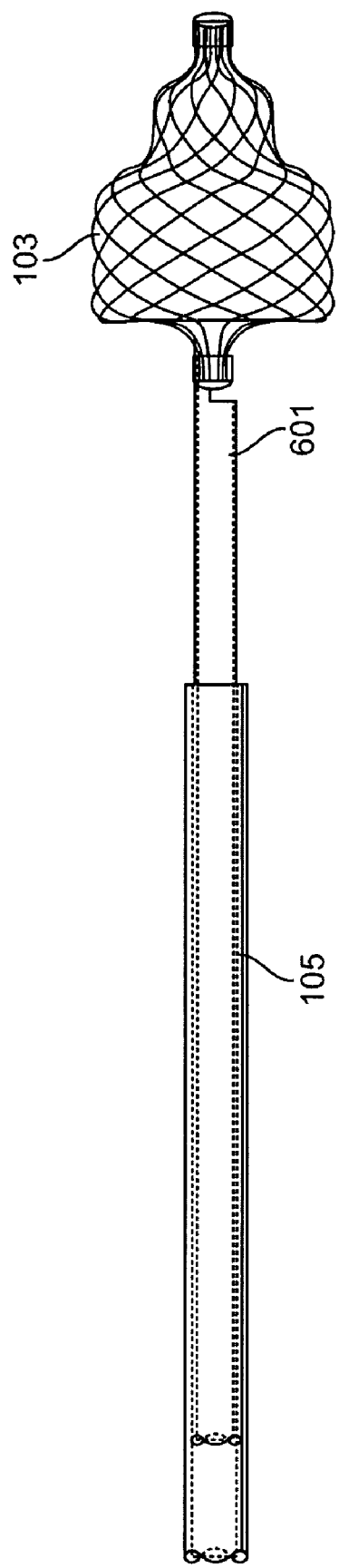

LOADING DEVICE FOR A PULMONARY IMPLANT

CROSS-REFERENCES TO RELATED APPLICATIONS

This application claims priority to U.S. Provisional Patent Application No. 60/893,940, filed on Mar. 9, 2007, the full disclosure of which is incorporated herein by reference.

BACKGROUND OF THE INVENTION

1. Field of the Invention

This invention relates generally to implants, and specifically to devices for loading a collapsible implant onto a delivery catheter, and more particularly for loading a collapsible pulmonary implant onto a delivery catheter.

2. Description of the Background Art

Collapsible self-expanding implants are well known in the medical device field. Historical medical uses for such implants include maintaining openings in vascular, urinary, biliary, esophageal, and renal tracts, and vena cava filters. Recently, modified pulmonary implants are being contemplated for the treatment of pulmonary disorders. Some such pulmonary devices differ from conventional occlusive devices in that they are designed to constrict, block, or significantly restrict fluid flow in a pulmonary passageway, rather than maintain an opening in it.

Self-expanding pulmonary implants must be compressed to enable delivery through relatively small and curved body pathways. A delivery device, such as a delivery catheter, retains the pulmonary implant in its radially compressed state as it transports the implant to a treatment site through relevant bodily passageways. There, the implant is released and expands to its non-compressed shape.

One of the challenges for the delivery of such pulmonary implants is accurately loading the implant onto the delivery catheter without dropping or damaging the device. The physician or nurse attempting to load the implant onto the catheter often finds it difficult to perform the task. Therefore, devices for loading implants onto delivery catheters are desirable.

Also, implants that are already pre-loaded onto a catheter might lose some of their functionality as they remain on the shelf for extended periods of time before they are used in a patient. Ideally, the device would be maintained in its native state until it is ready to be used in a patient. When ready to be used, the physician should be able to load the implant onto the delivery catheter using a simple maneuver. Furthermore, the implant should be well protected during shipping and transfer until it is ready to be used. A simple system that would meet all the above needs would be highly desirable.

U.S. Pat. No. 6,096,027 discloses an apparatus for loading a stent onto a catheter using a flexible sleeve to encase the stent as it is pulled through a tapered passageway. Commonly assigned published U.S. patent application No. 20060162731 A1 discloses a loading mandrel positioned within a loading body, wherein the loading mandrel is manipulated to load an occlusal stent into a wide-mouthed end of the loading body and move the occlusal stent to a narrow-mouthed end within the loading body.

BRIEF SUMMARY OF THE INVENTION

Devices for loading a collapsible implant onto a delivery catheter are disclosed. A loading device accepts a flexible and self-expanding implant, as well as the distal end of a delivery catheter. The loading device guides the implant through a narrowing passage that feeds into the distal end of the catheter. As the implant passes through the narrowing passage, it is compressed to a diameter that allows the implant to be inserted into the catheter.

In one aspect, a loading device comprises an outer tubular structure and an inner tubular structure. The outer tubular structure comprises a narrowing passage configured to receive a catheter at one end and a collapsible implant at another end. The inner tubular structure is configured to move slidably and co-axially within the outer tubular structure. The inner tubular structure comprises a carrier pin configured to move within the narrowing passage as the inner tubular structure slides into the outer tubular structure. The sliding of the inner tubular structure into the outer tubular structure causes an implant mounted on the carrier pin to collapse as the implant moves through the narrowing passage and into the distal end of a catheter. Optionally, the outer tubular structure further comprises a grasper to stabilize the catheter for receipt of the collapsible implant, and the internal diameter of the inner tubular structure varies to cause the grasper to first contract and stabilize the catheter, and then expand and release the catheter, as the grasper moves into the inner tubular structure.

In another aspect, the loading device comprises an outer shaft comprising a narrowing passage leading to an opening for receiving the distal end of a catheter, an opening for accepting a collapsible implant, and two compression members. The first compression member is configured to move slidably within the outer shaft and guides the implant through the narrowing passage, thereby collapsing it. The second compression member then inserts the implant into the catheter.

In another aspect, the loading device comprises two tubular structures with opposing narrowing inner diameters, with one tubular structure configured to move slidably over the other. Placement of an implant between the structures, followed by sliding one tubular structure over the other, causes the implant to radially compress within the two opposing narrowing cavities.

In another aspect, a catheter with a slotted rod is configured to hold and pull a collapsible implant through a narrowing passage and into the distal opening of the catheter. In another aspect, the slotted rod comprises a spring loaded ball configured to increase the grip on the implant. In another aspect, the rod comprises a grasping or latching mechanism configured to latch onto the implant as the implant is pulled through the narrowing passage and into the catheter. In another aspect, the rod comprises a loop wire configured to secure the implant as the implant is pulled through the narrowing passage and into the catheter. The loop wire may comprise shape-memory material such as Nitinol to allow it to release the implant by increasing the slack in the loop wire.

The present invention further provides sterile kits for distributing and storing the system components. The kits will include packaging for holding the components, usually including a primary package which may be a box, pouch, cylinder, or other protective package. The individual system components are usually held within separate sterile containers within the primary package, usually being in pouches, cylinders, or the like. As a particular advantage of the present invention, self-expanding implants may be preloaded within the loading device and held in their uncollapsed configuration, thus reducing the risk of damaging the elastic implant materials prior to loading and implantation. Optionally, the kits may comprise instructions for use setting forth any of the loading methods described herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 1a-1g show a loading device, in accordance with a first embodiment of the present invention.

FIGS. 3a-3e show a loading tool according to yet another embodiment of the present invention.

FIGS. 4a-4e illustrate a catheter with a slotted rod configured to hold and pull on the proximal end of a compressible implant.

DETAILED DESCRIPTION OF THE INVENTION

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

Various embodiments of a loading device are disclosed for loading a collapsible pulmonary implant onto a delivery system, in preparation for delivering the implant into the pulmonary airways of a patient. The delivery system may comprise a catheter. Collapsible pulmonary implants are made of memory-shape materials, such as Nitinol, and are compressed to enable delivery through relatively small and curved bodily pathways to the treatment site. Delivery devices, such as catheters, retain the collapsed pulmonary implants in a radially compressed state for delivery to the treatment site, where the implant is released into the airway and regains its non-compressed shape. The present invention discloses various embodiments of a loading device that collapses such implants and optionally inserts them onto a delivery catheter. The present invention further discloses various embodiments of catheters comprising rods for securing and pulling a collapsible pulmonary implant through a narrowing passage and into the catheter, collapsing the implant before it enters the catheter. As should be obvious to one of ordinary skill in the art, the present embodiments can be used with any implants that are delivered bronchoscopically for inducing atelectasis. Such implants may be restrictive or occlusive in nature, or valve-based.

FIGS. 1a-1g illustrate a loading device 100 according to a preferred embodiment of the present invention.

Figure 1A:
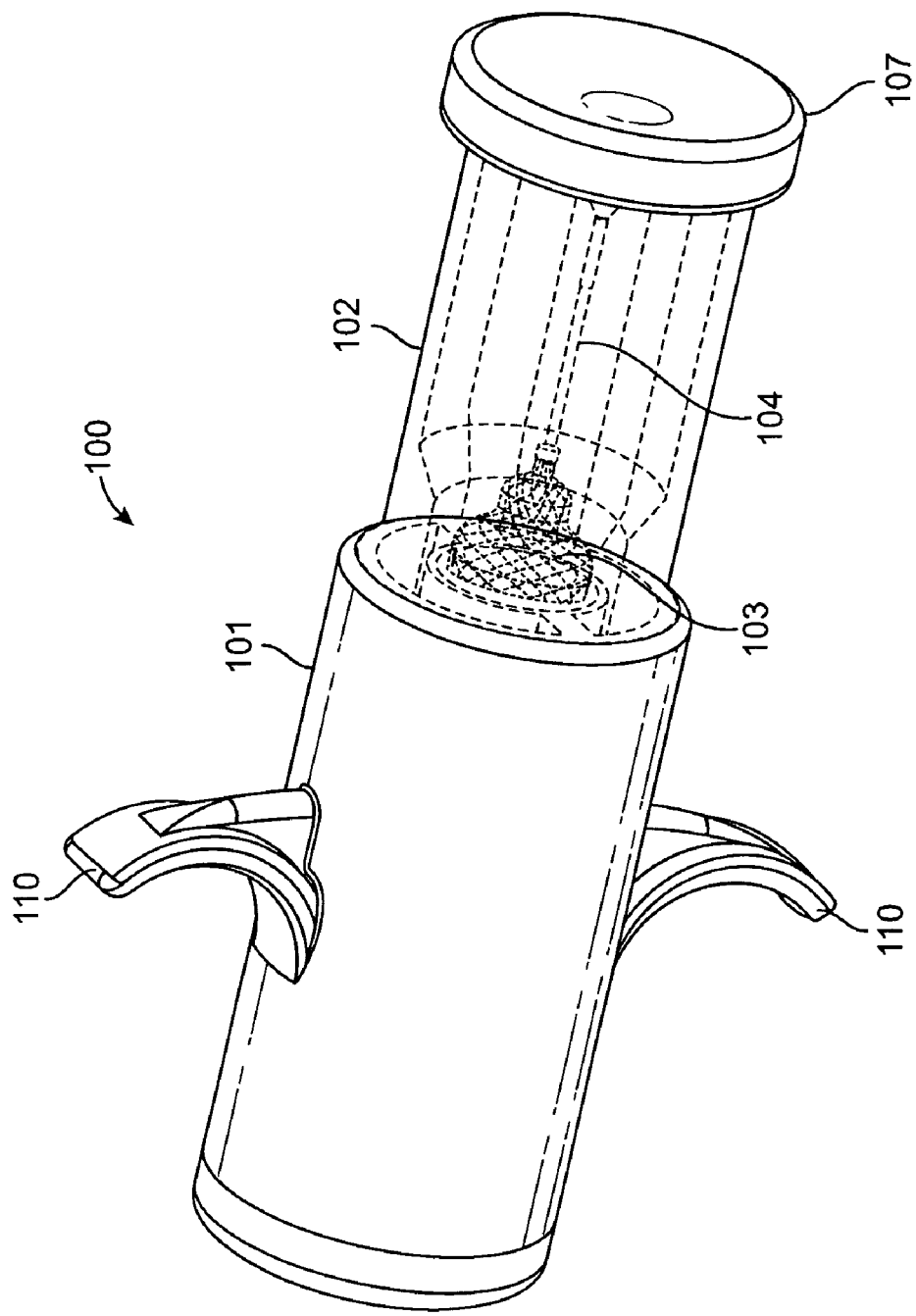

FIG. 1a shows the assembled loading device 100. An inner tubular structure 102 is configured to move slidably into and out of an outer tubular structure 101. The inner tubular structure 102 is hereinafter also referred to as a plunger 102, and the outer tubular structure 101 is hereinafter also referred to as a barrel 101.

The plunger 102 comprises an optional cap 107. A carrier pin 104 may be attached to the plunger 102 itself, or alternatively attached to the cap 107 as is shown in the Figures. A collapsible pulmonary implant 103 is mounted on the carrier pin 104, positioned for compression through a narrowing passage and insertion into a catheter. One end of the barrel 101 is configured to receive the implant 103 mounted on the carrier pin 104, and the other end is configured to receive a catheter (as is shown in the additional figures below). As the plunger 102 slides into the barrel 101, the carrier pin 104 guides the implant 103 through the narrowing passage 106, compressing the implant 103 and inserting it into the opening at the distal end of the catheter.

The barrel 101 comprises optional finger rests 110. Finger rests 110 and cap 107 allow a user to place two fingers in the finger rests 110 and hold the loading device 100 while using the thumb or the palm of the hand to slide the plunger 102 into the barrel 101, similar to using a syringe or a pump, as shown in FIG. 1e.

Figure 1B:
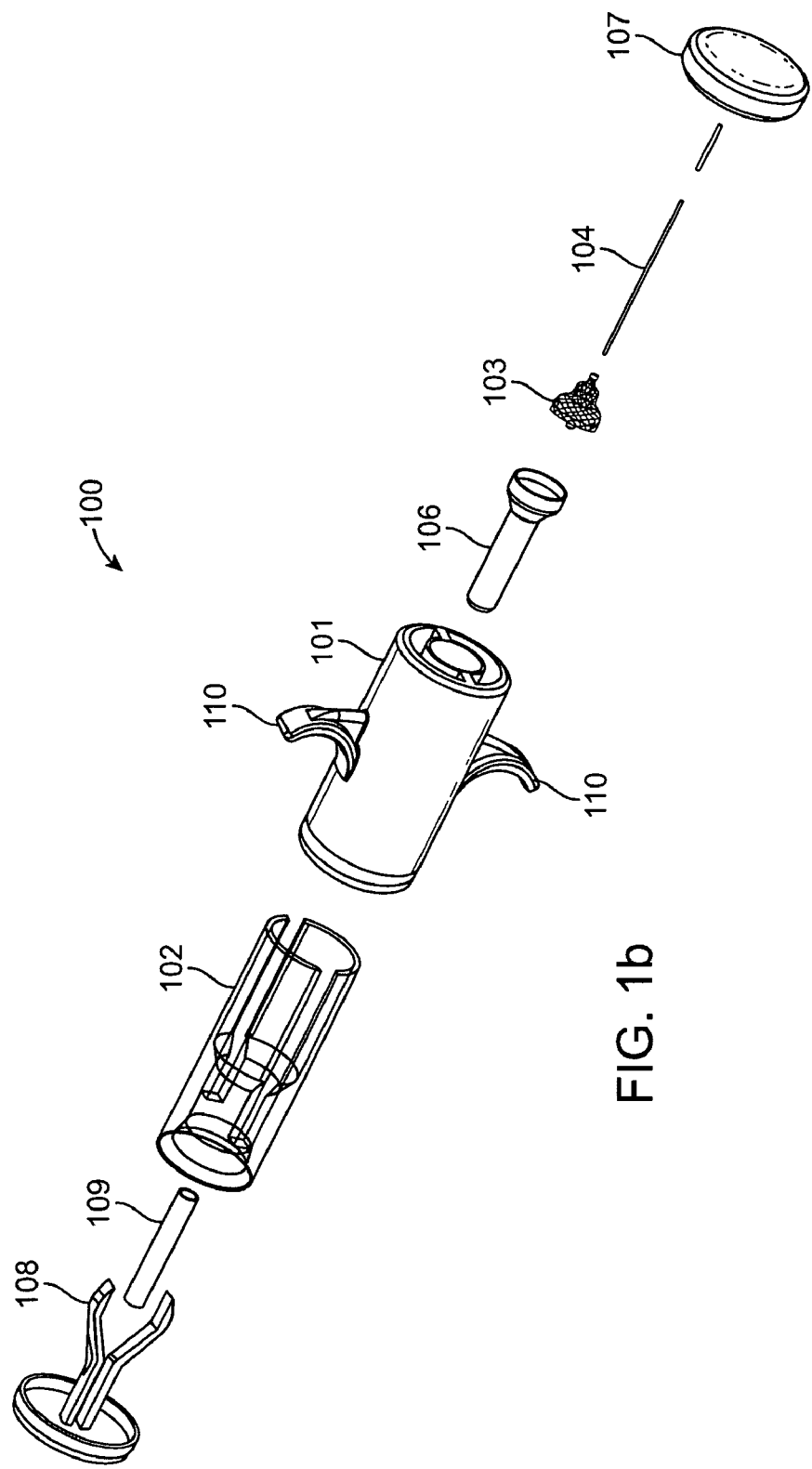

FIG. 1b shows an exploded view of the components of the loading device 100, showing the barrel 101 with optional finger rests 110, the plunger 102, a cap 107, a carrier pin 104, a narrowing passage 106, a catheter passage 109, an optional grasper 108, and a collapsible implant 103.

Figure 1C:
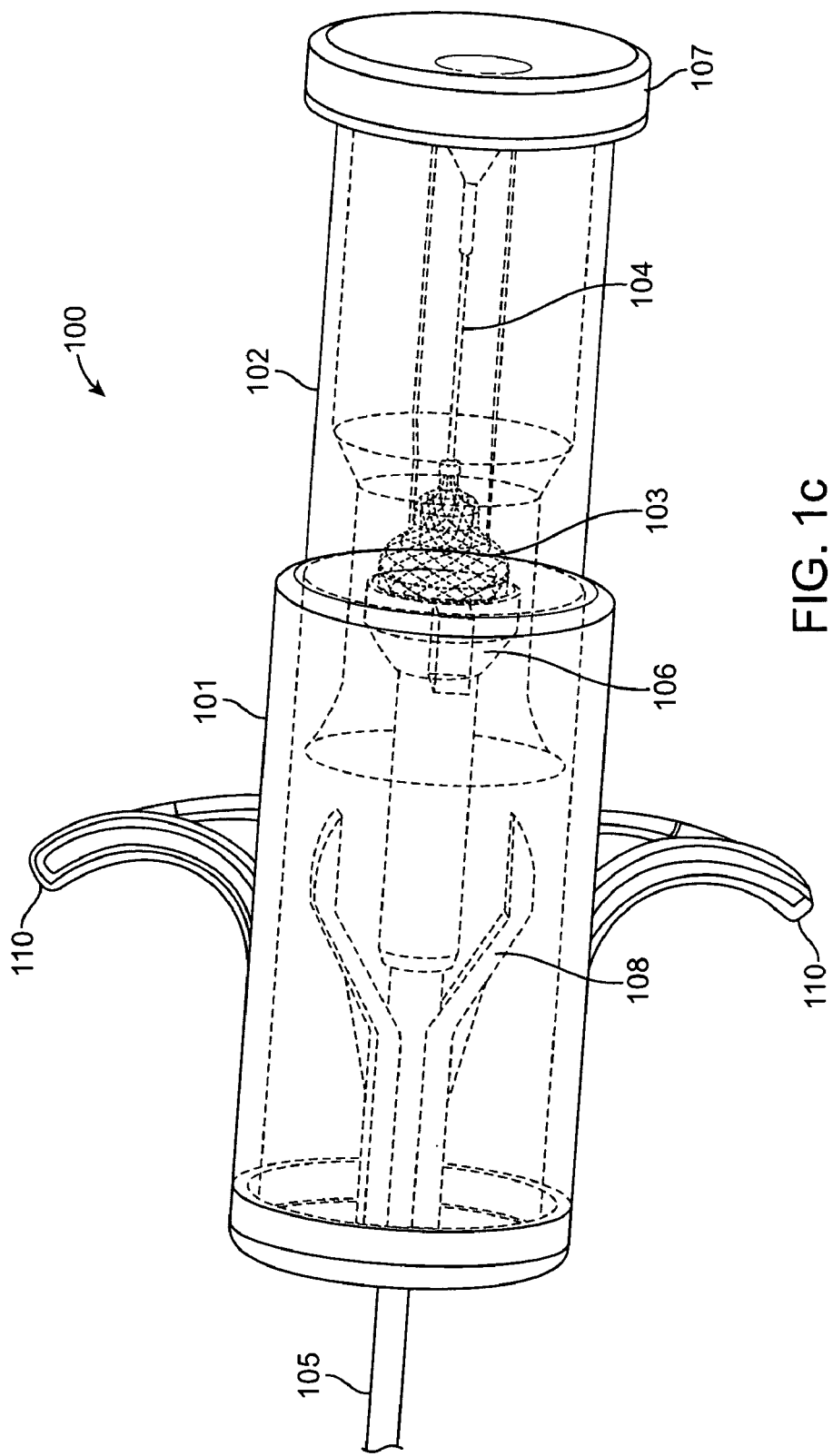
Figure 1D:
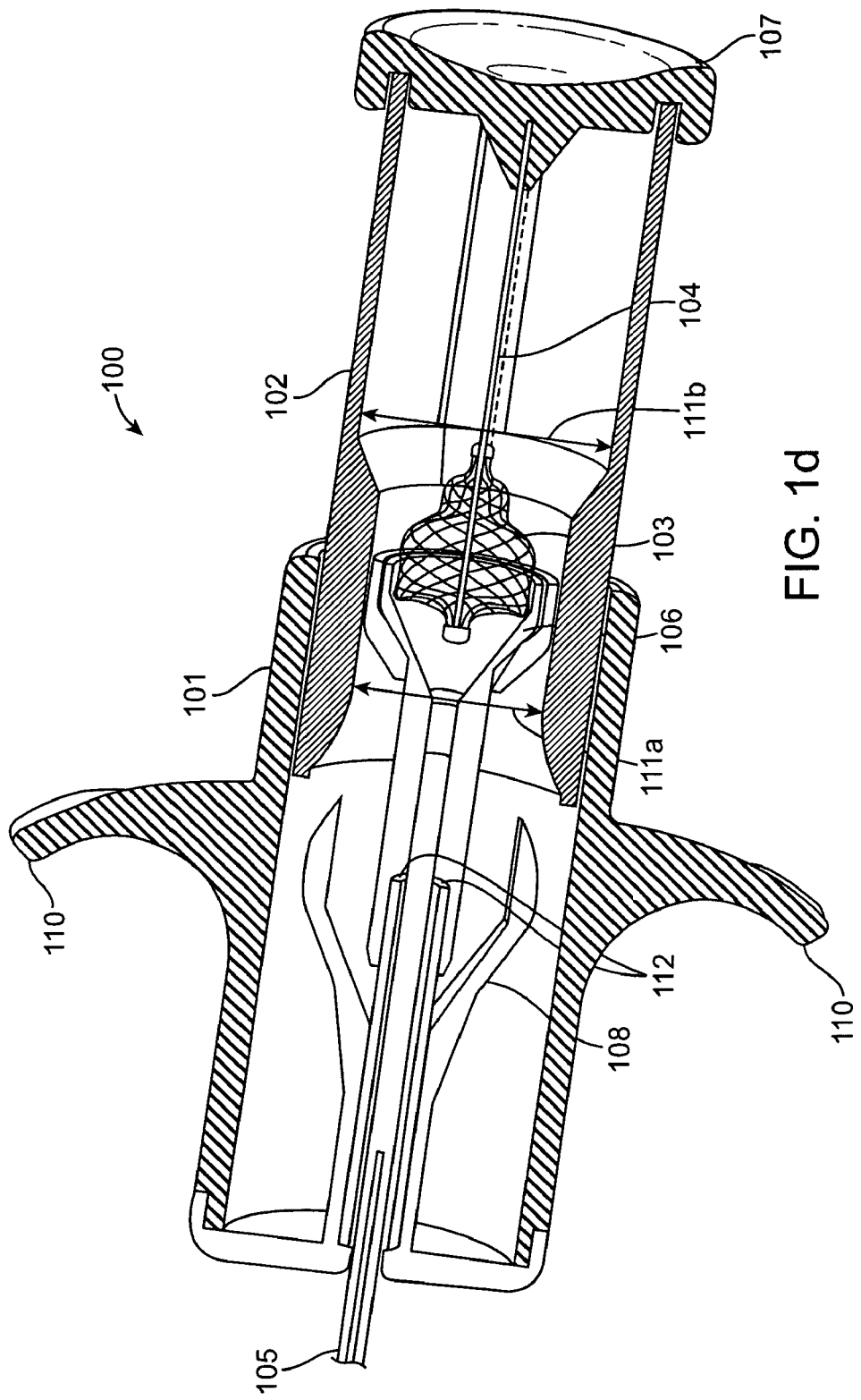
Figure 1E:
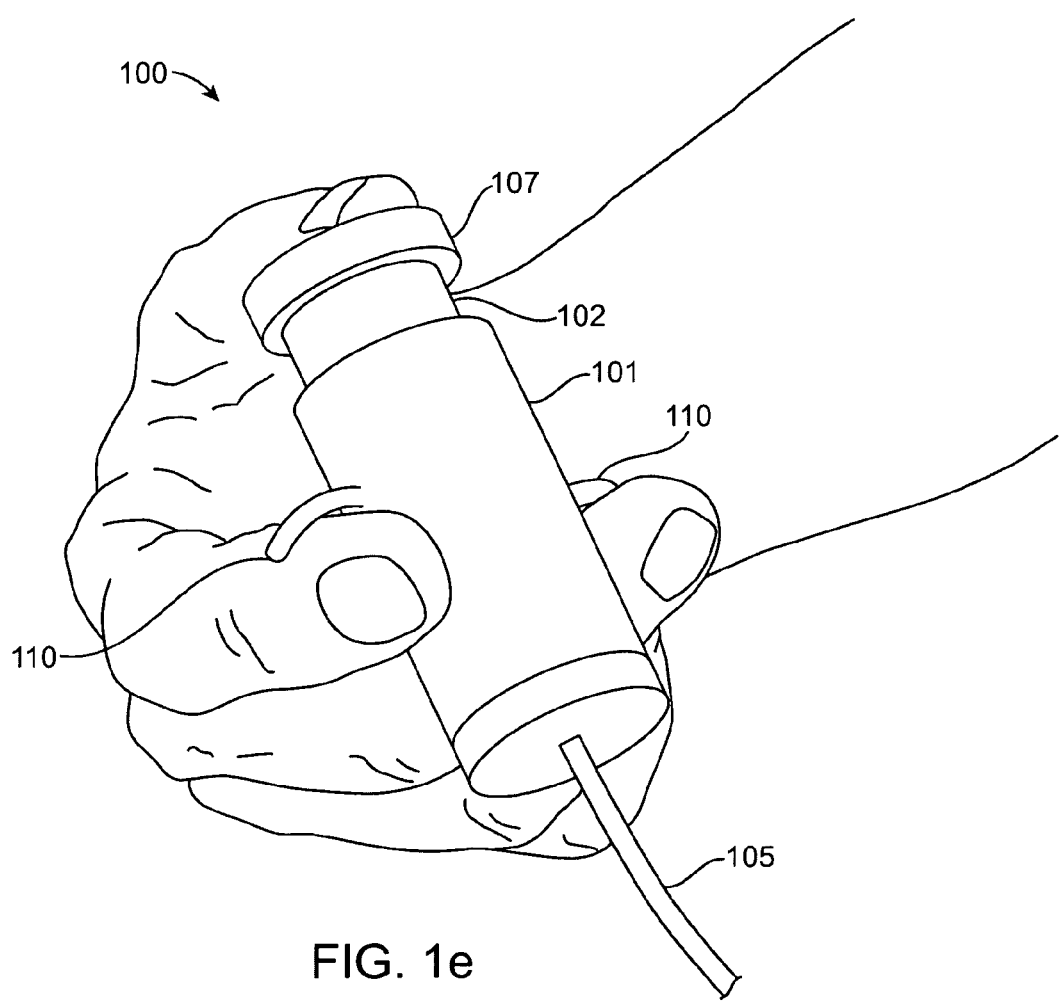

FIGS. 1c and 1d show interior and cross-sectional views of the loading device 100, with a catheter 105 inserted into the loading device 100. As shown, the loading device 100 comprises a narrowing passage 106. Movement of the implant 103 into the narrowing passage 106 compresses the implant 103, thereby reducing its diameter until the diameter is small enough to fit into the catheter 105. A continuation of the same plunging motion that compresses the implant 103 also inserts it into the catheter 105. As shown in FIG. 1d, the catheter 105 comes to rest as it comes in contact with indentations 112. A user compresses the loading device, as shown in FIG. 1e, thereby causing tubular structure 102 to move into tubular structure 101.

Still referring to FIGS. 1c and 1d, the loading device 100 optionally comprises a grasper 108. The grasper 108 is configured to grasp down on an inserted catheter 105 upon application of a force, which is provided by the tapered cavity of the plunger 102. This cavity comprises a first section with a reduced internal diameter 111a and a second section with a larger internal diameter 111b, as depicted in FIG. 1d.

Prior to the plunger 102 sliding into the barrel 101, the grasper 108 is in an open, released state. The sliding of the plunger 102 into the barrel 101 forces the grasper 108 through the reduced diameter section of the plunger 102 and causes the grasper 108 arms to close. As a result, the grasper 108 grasps and holds down the catheter 105, thereby stabilizing the catheter 105 for the insertion of the compressed implant 103 during the movement of the loading device 100. Upon moving through and exiting the reduced diameter section of the plunger 102 and entering the larger diameter section, the grasper 108 arms return to their open state, thereby releasing the loaded catheter 105 and allowing a user to remove the catheter 105 from the loading device 100.

Figure 1F:
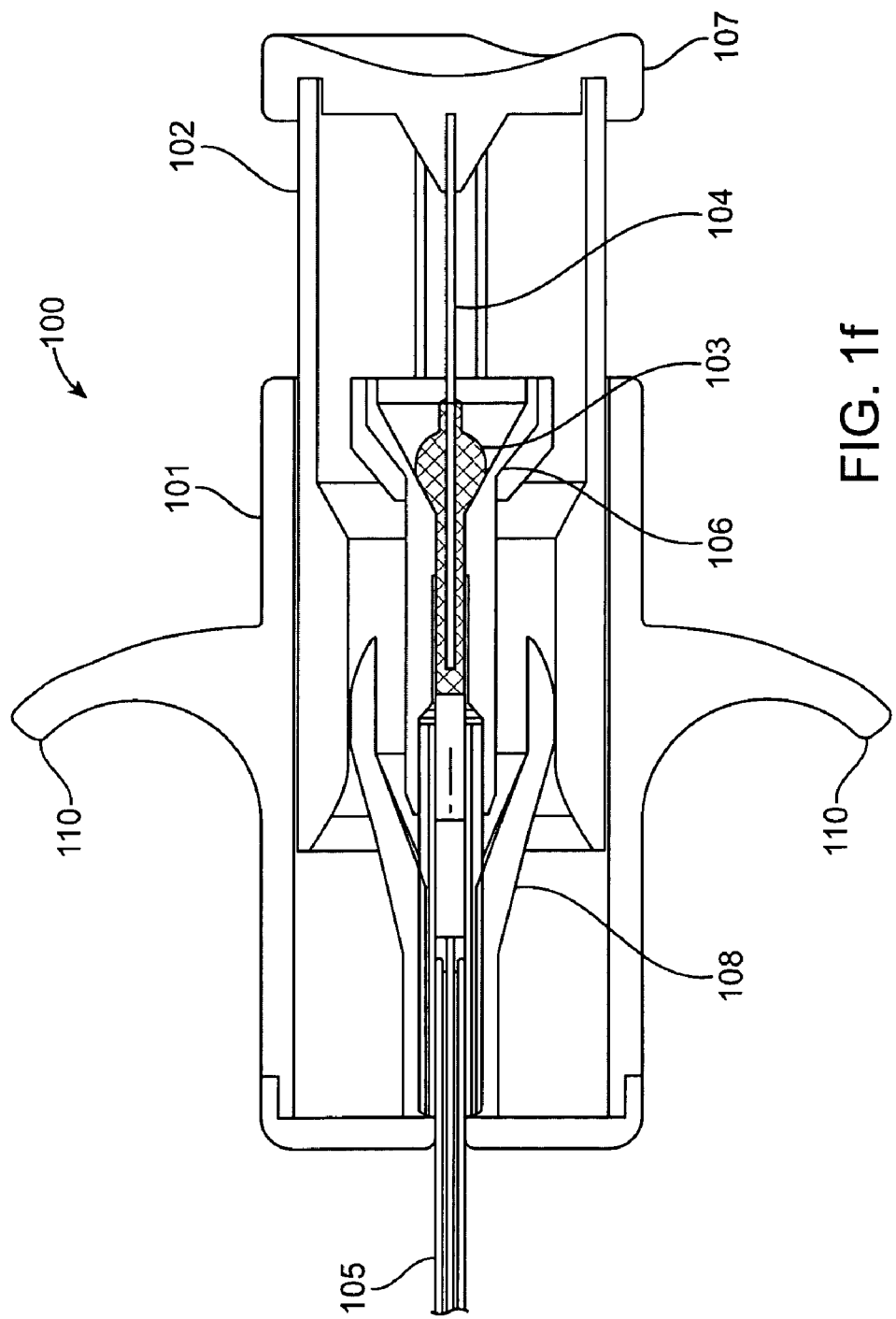

FIG. 1f shows the loading device 100 in a partially compressed state. The plunger 102 has moved into the tubular structure 101, and the carrier pin 104 has guided the implant 103 through the narrowing passage 106 and compressed it. FIG. 1g shows the loading device 100 in a fully compressed state. When the loading device 100 is fully compressed, i.e., the plunger 102 has completed its travel from the proximal end of the barrel 101 to the distal end of the barrel 101, the implant 103 has been inserted into the catheter 105, and the grasper 108 has released the catheter 105 after passing through the reduced diameter section of the plunger 102. In other words, the loading device 100 has, in one continuous motion, grasped (stabilized) the delivery catheter 105, loaded the implant 103 onto the catheter 105, and released the catheter 105 when the implant 103 has been loaded. This enables the user to conveniently load an implant 103 with the least amount of effort and ensure that it is loaded properly.

Optionally, the loading device 100 is configured to allow a user to visually verify that the implant 103 is loaded onto the catheter 105. For example, in one embodiment the plunger 102 and/or barrel 101 may comprise at least partially transparent material, such as glass or plastic. In another embodiment, the device 100 may comprise a cut-away portion serving as a viewing port.

It is an advantageous aspect of the loading device 100 that it allows for loading the implant 103 at an accurate and predictable location within the catheter 105. It is another advantageous aspect of the loading device 100 that it facilitates simple, straightforward, repeatable operation, providing ease of use. It is yet another advantageous aspect of the loading device 100 that it prevents damage to the implant 103 during shipping, storage, and loading operation. It is yet another advantageous aspect of the loading device 100 that it prevents the implant 103 from resting on its side over an extended period of time, thereby preventing damage to, or functional degradation of, the implant 103. One of the most important advantages offered by the loading device 100 is that it prevents insertion of the implant 103 onto the catheter 105 in an incorrect (i.e., reversed) distal-proximal orientation. It is yet another advantageous aspect of the loading device 100 that it can be sterilized together with the implant 103 and separately from the catheter 105. It is yet another advantageous aspect of the loading device 100 that it prevents damage to the catheter 105 during loading. The loading device 100 may be made of light-weight materials, as well as an intuitive form factor, and thus making it easy it to handle.

Figure 2:
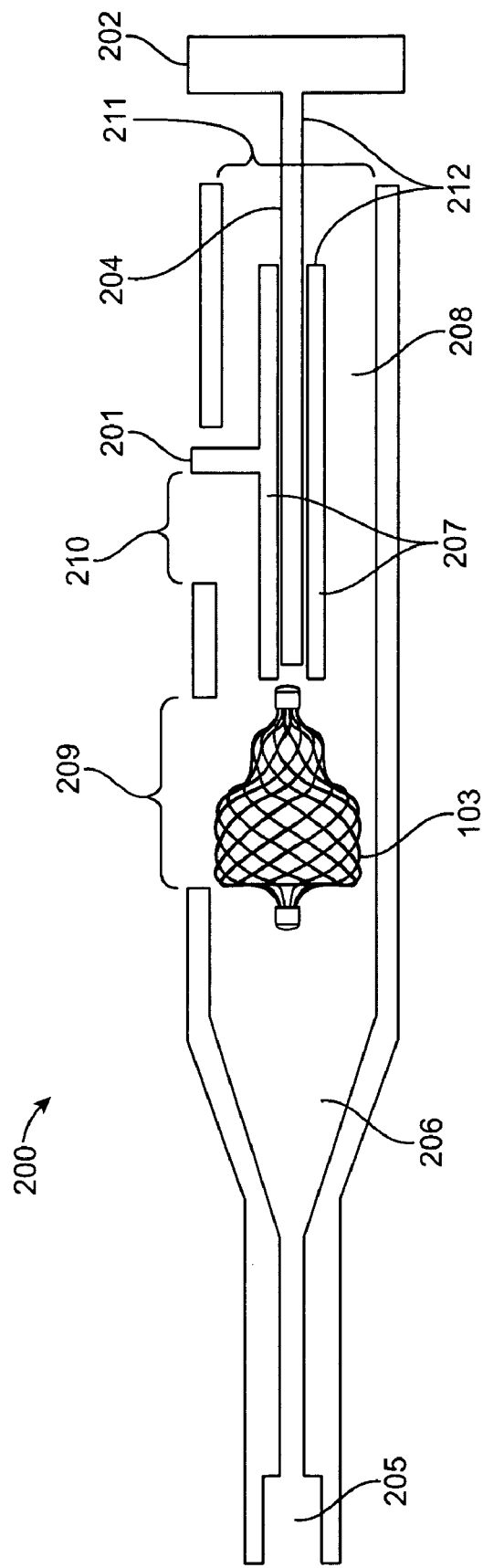
FIG. 2 shows an alternative embodiment of the loading tool according to the present invention.

FIG. 2 shows a loading device 200 according to a second alternative embodiment of the present invention. Loading device 200 comprises an elongate outer shaft 208 comprising a narrowing passage 206 leading to an opening 205 for receiving the distal end of a catheter (not shown). The loading device 200 comprises a first stage compression member 207 configured to move slidably within the outer shaft 208, and a second stage compression member 204 configured to move slidably within the first stage compression member 207.

The first stage compression member 207 comprises a handle 201 protruding through an opening 210 on the side of the outer shaft 208. The second stage compression member 204 comprises a handle 202 protruding through an opening 211 of the outer shaft 208. The two compression members 207 and 204 are connected to each other via a tether 212.

To load a implant 103 onto a catheter 105 using the loading device 200, the implant 103 is inserted into through an opening 209 into the loading device 200, and the distal tip of a catheter 105 is inserted into the opening 205. The catheter's tip is secured to the loading device 200 prior to insertion of the implant 103.

Once the catheter tip is inserted into and secured to the loading device, a user uses handle 201 to slide the first stage compression member 207 towards the narrowing passage 206. The first stage compression member 207 guides the implant 103 through the narrowing passage 206, thereby compressing the implant 103. When the first stage compression member 207 completes its range of motion, the implant 103 is sufficiently compressed to allow the second stage compression member 204 to insert the implant 103 into the catheter 105. Since the two compression members are tethered together, the second stage compression member 204 follows as the first stage compression member 207 completes its range of motion. At that point, the user uses the handle 202 to slide the second stage compression member 204 forward, guiding the now compressed implant 103 through the remainder of the narrowing passage 206 and into the opening at the distal end of the catheter 105.

Figure 3B:
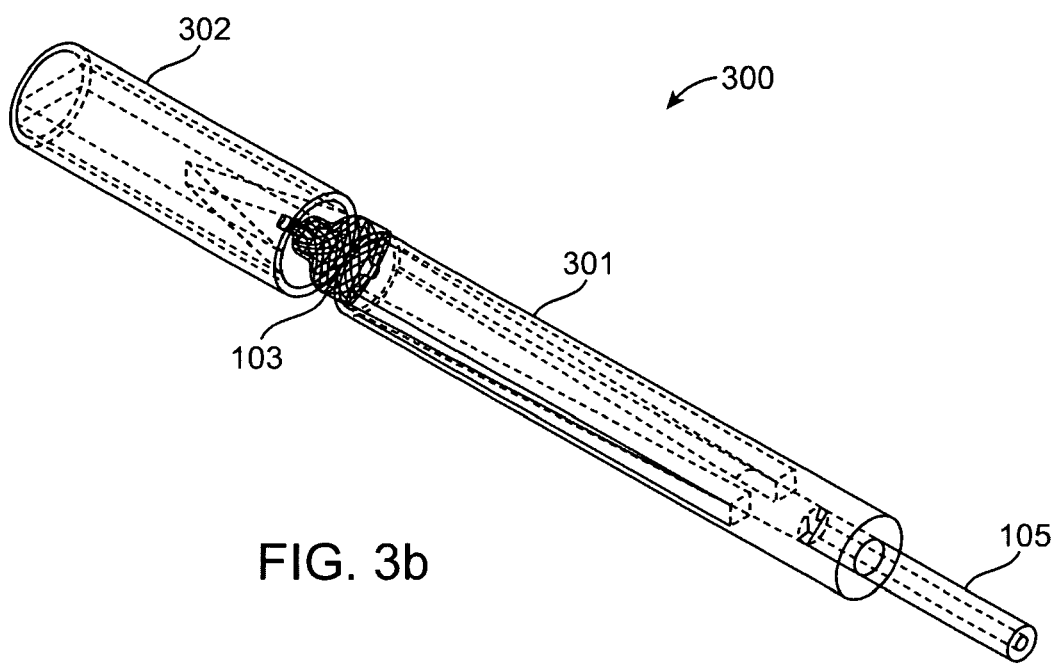

FIGS. 3a-3e show a loading device 300 according to a third alternative embodiment of the present invention. Referring to FIG. 3a, the loading device 300 comprises two tubular structures 301 and 302, with tubular structure 302 configured to move slidably over tubular structure 301. The tubular structures 301 and 302 each have a narrowing inner cavity, with opposing directions of narrowing, as can be seen in FIG. 3b. Tubular structure 301 has an opening for insertion of a catheter 105. Placement of the implant 103 between tubular structures 301 and 302, followed by the sliding of tubular structure 302 over tubular structure 301, causes the implant 103 to radially compress within the two opposing narrowing cavities and slide into the catheter 105.

Figure 3C:
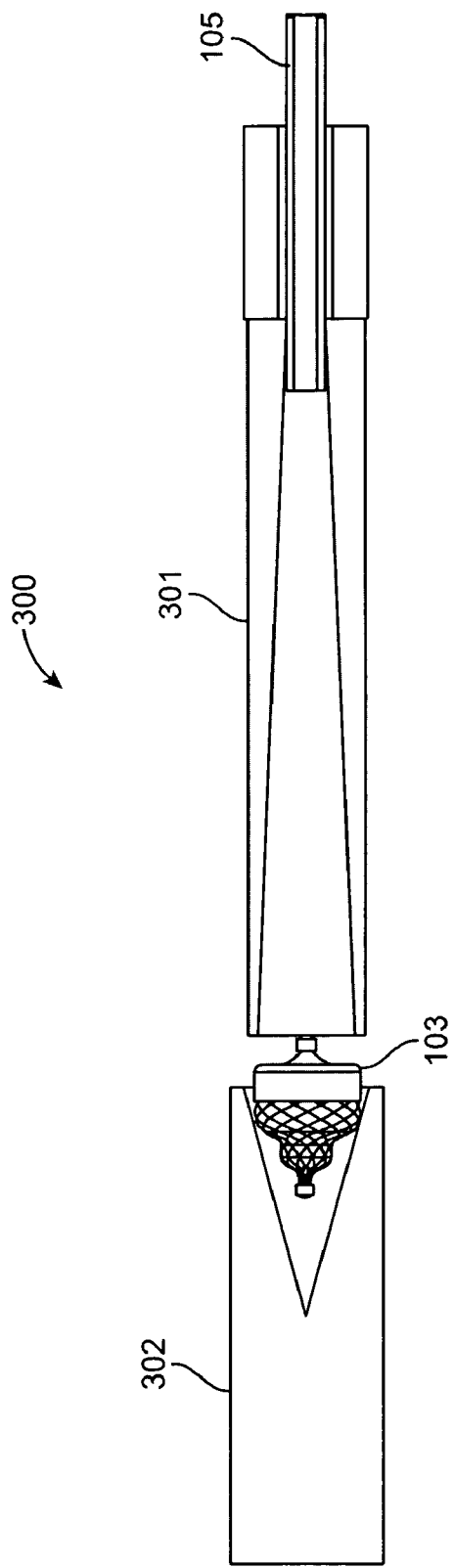
Figure 3D:
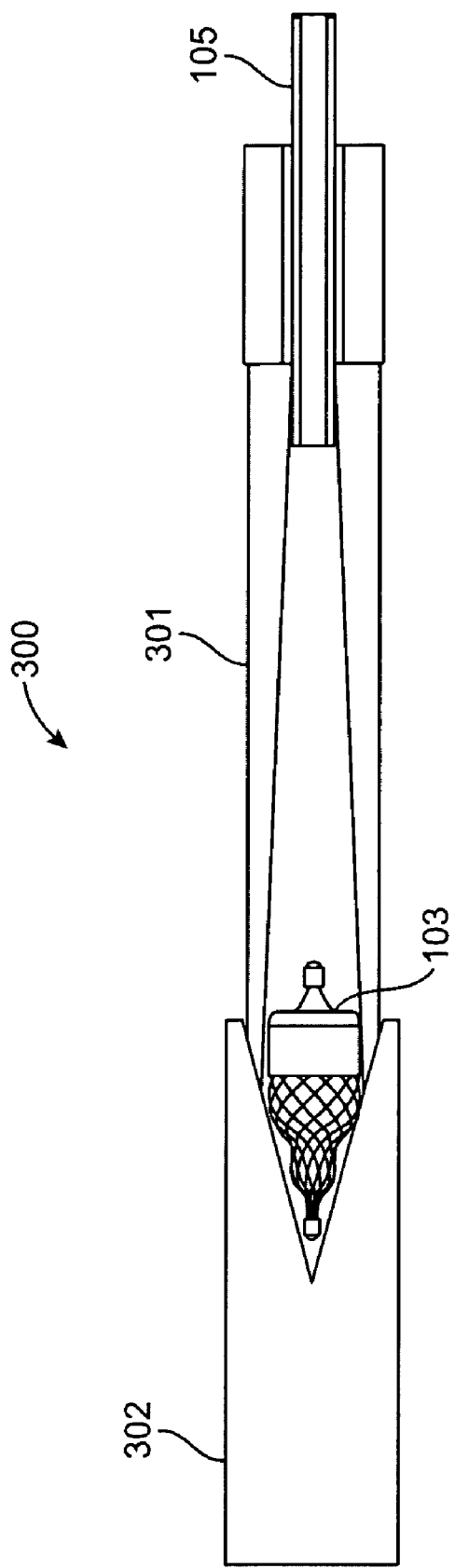
Figure 3E:
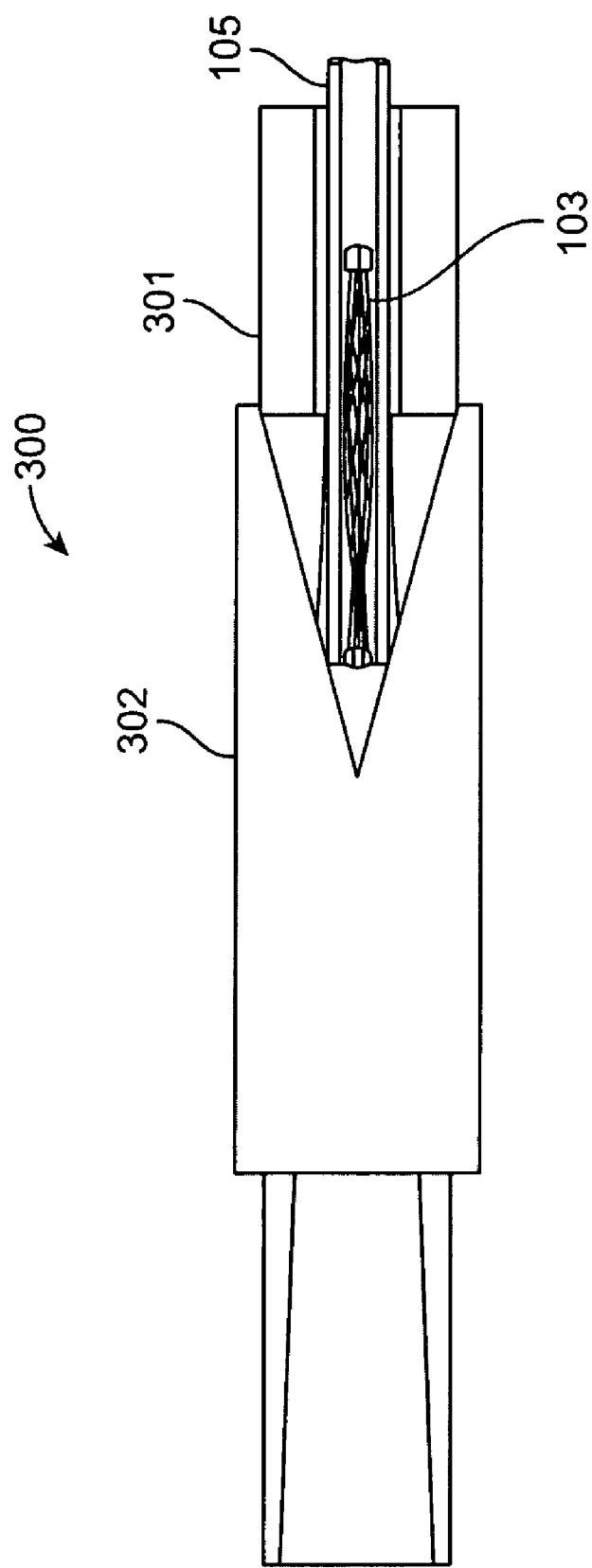

FIG. 3c shows a cross-sectional view of the separated tubular structures 301 and 302. Once the tubular structures 301 and 302 are separated, the user positions a implant 103 between them and slides tubular structure 302 over tubular structure 301 to compress the implant 103 and insert it into the catheter 105, as seen in FIGS. 3d and 3e.

FIGS. 4a-4e, 5, 6 and 7 show catheter 105 comprising members for loading an uncompressed implant 103 onto the catheter 105, in accordance with embodiments of the present invention. In these embodiments, the catheter 105 comprises a lumen or sheath, and a member within the lumen or sheath that extends distally out of the catheter 105 and attaches itself to an uncompressed implant 103, pulls the implant 103 through a narrowing passage to compress the implant 103, and then continues to pull the now compressed implant 103 into the catheter 105. We now turn to describing the various embodiments.

FIGS. 4a-4e illustrate a catheter 105 with a slotted rod 601 configured to hold the proximal end (such as a bushing) of a compressible implant 103, in accordance with an embodiment of the present invention. The catheter is inserted through a narrowing passage 602. In the embodiments described herein, the rod may be a hypotube, a coil, a solid wire, or any other such element that can be rigid.

Figure 4C:
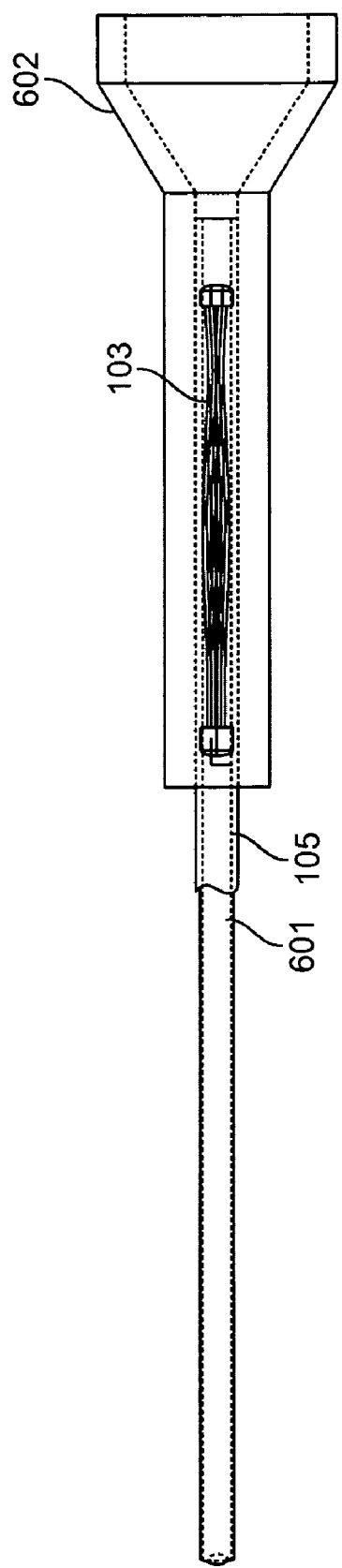

Referring to FIG. 4a, the slotted rod 601 is extended distally out of its encasing catheter 105. Referring to FIG. 4b, the uncompressed implant 103 is placed within the slot. The slotted rod 601 then pulls the implant 103 through the narrowing passage 602 and compresses it (not shown) to a diameter that is small enough to be inserted into the internal lumen of the catheter 105. Finally, the collapsed implant 103 is pulled into the catheter 105, as shown in FIG. 4c.

Figure 4E:
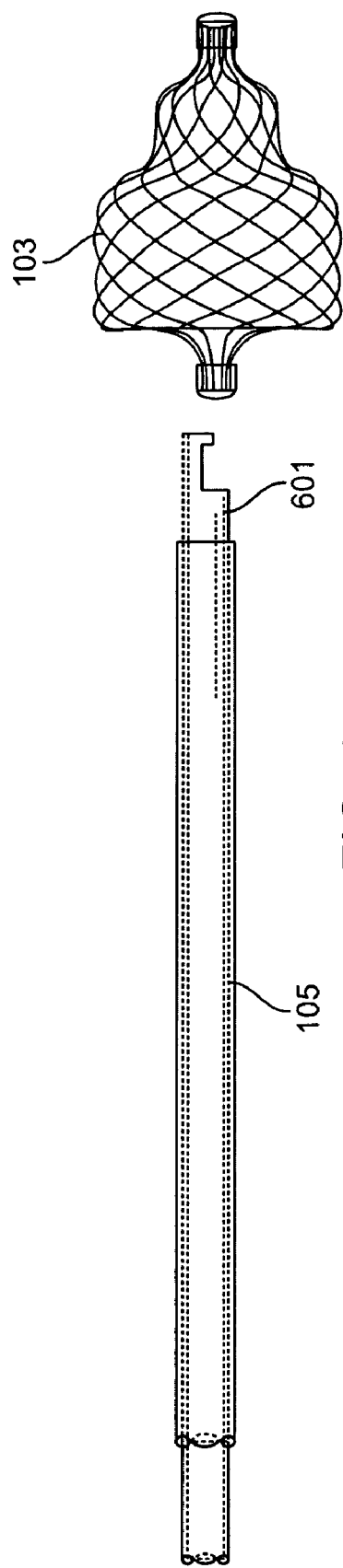

Once compressed and stored within the catheter 105, the implant 103 can be released from the catheter 105 by extending the rod 601 distally out of the catheter 105, or alternatively by pulling the catheter lumen or sheath back to expose the rod 601. Referring to FIGS. 4d and 4e, once the implant 103 has been deployed into the bronchial passageway of a patient, the user can twist or turn the rod 601 and disengage the implant 103.

Figure 5:
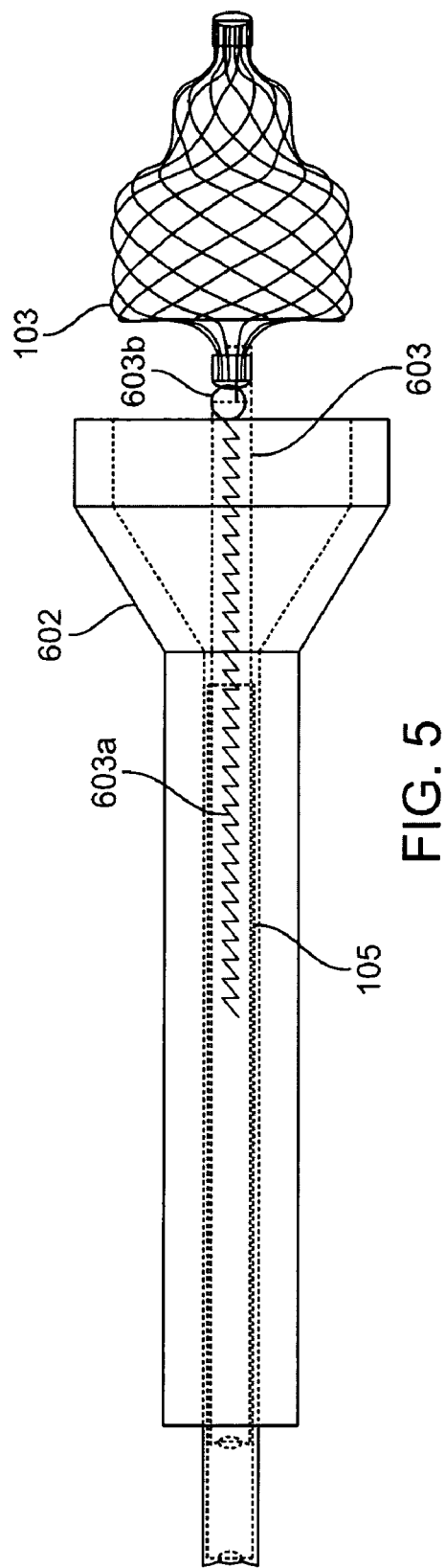
FIG. 5 illustrates a catheter with a rod comprising a spring loaded ball to increase the grip on a compressible implant.

In an optional embodiment, the rod may comprise a mechanism for more tightly gripping the implant 103. Referring to FIG. 5, a rod 603 is shown comprising a spring 603a and a spring loaded ball 603b to increase the grip on the implant 103. Referring to FIG. 5, the slotted rod 603 is pushed out of its catheter (not shown). To load the implant 103, the bushing of the implant 103 is placed within the slot and the spring loaded ball 603b exerts a gripping pressure against the implant 103, holding it tightly in place. The implant 103 is then pulled into the narrowing passage 602 and compressed to a diameter smaller than that of the internal lumen of the catheter (not shown) and further pulled into the catheter. Once compressed, the implant 103 can be released again from the catheter by pushing the rod 603 out of the catheter, or alternatively by pulling the catheter lumen or sheath back to expose the rod 603. As described above, once the implant 103 has been deployed into the bronchial passageway of a patient, the user can twist and turn the rod 603 to disengage the implant 103.

In an alternative embodiment, the rod may comprise an attachment mechanism such as a latch mechanism to latch onto the implant 103.

Figure 6:
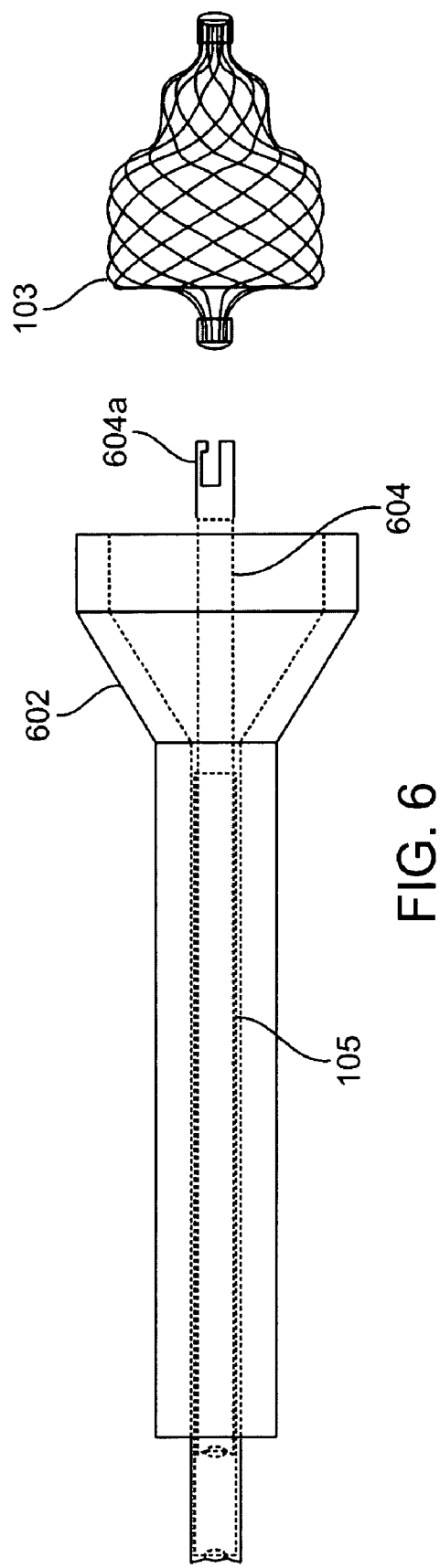
FIG. 6 illustrates a catheter with a rod comprising a latch mechanism to secure and pull a compressible implant.
Figure 7:
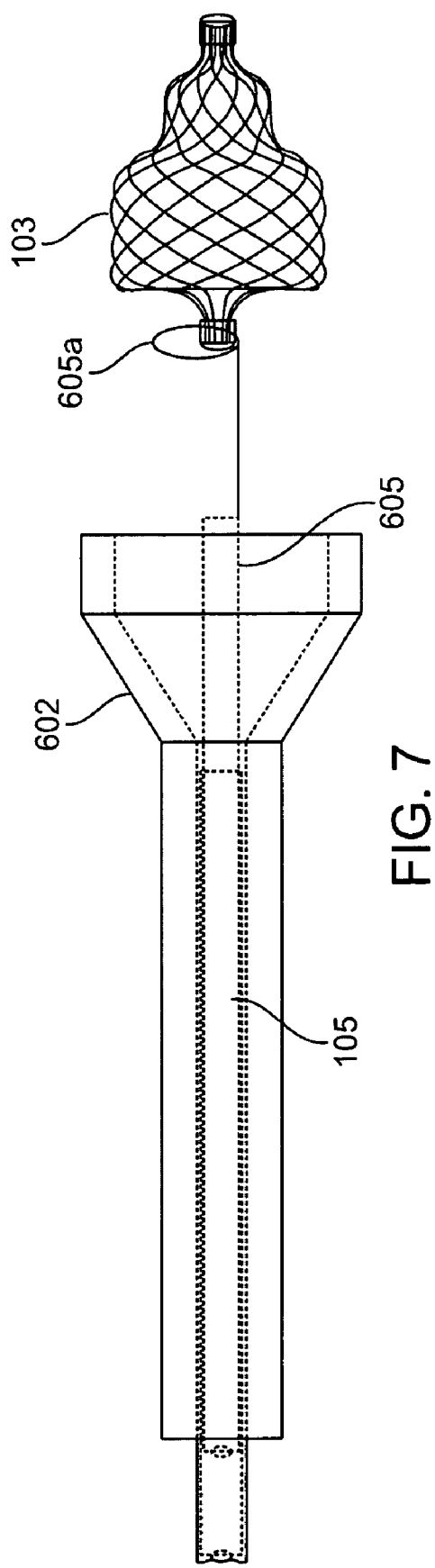
FIG. 7 illustrates a catheter with a rod comprising a loop wire to secure and pull an implant.

Referring to FIG. 6, the rod 604 comprises a latch 604a and is extended distally out of its encasing catheter 105. To load the implant 103, the bushing of the implant 103 is placed within the latch 604a and locked into place. As above, the implant 103 is then pulled through the narrowing passage 602 and compressed to a diameter smaller than that of the internal lumen of the catheter 105. Once compressed, the implant 103 can be released again from the catheter 105 by pushing the rod 604 out of the catheter 105 (or alternatively by pulling the catheter lumen or sheath back to expose the rod 604) and releasing the latch 604a. Once the implant 103 has been deployed into the bronchial passageway of a patient, releasing the latch 604a causes the rod 604 to disengage from and release the implant 103.

In an alternative embodiment, the rod may comprise a loop wire as an attachment mechanism to secure the implant 103 to the rod. This is illustrated in the embodiment shown in FIG. 7. The rod 605 comprises a loop wire 605a that protrudes out of its encasing catheter 105 and loops around the bushing of the implant 103, pulling the implant 103 into the narrowing passage 602 and compressing it to a diameter smaller than that of the internal lumen of the catheter 105. The loop wire 605a may comprise shape memory material such as Nitinol to allow it to release the implant 103 by increasing the slack in the loop wire 605a.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for loading a flow restrictive, collapsible pulmonary implant into a delivery catheter, the system comprising:
 a loading device; a delivery catheter; and a flow restrictive, collapsible pulmonary implant;
 the loading device comprising:
 an outer tubular structure with a distal end and a proximal end, the outer tubular structure comprising:
 a narrowing passage with an opening disposed at the proximal end of the outer tubular structure to accept the collapsible pulmonary implant, wherein the narrowing passage narrows in a proximal-to-distal direction;
 a catheter passage in communication with the narrowing passage and having an opening at the distal end of the outer tubular structure to accept a distal end of the delivery catheter; and
 at least one structure for stopping advancement of the distal end of the catheter through the catheter passage; and
 an inner tubular structure configured to be pushed into the proximal end of the outer tubular structure, the inner tubular structure comprising a carrier pin configured to hold the collapsible implant and advance the implant through the narrowing passage and into the distal end of the delivery catheter as the inner tubular structure slides into the outer tubular structure,
 wherein movement of the inner tubular structure into the proximal end of the outer tubular structure causes the implant mounted on the carrier pin to collapse as it moves through the narrowing passage and into the distal end of the catheter;
 the delivery catheter, having a diameter to allow it to pass into the catheter passage of the loading device via the opening at the distal end of the passage; and
 the flow restrictive, collapsible pulmonary implant, housed in an uncollapsed configuration within the inner tubular structure of the loading device and mounted on the carrier pin.

2. The system of claim 1, wherein the device is configured to allow a user to visually verify that the implant is loaded onto the catheter.

3. The system of claim 2, wherein the device comprises at least partially transparent material.

4. The system of claim 2, wherein the device comprises a viewing port.

5. The system of claim 1, wherein the outer tubular structure further comprises a grasper to stabilize the catheter for receipt of the collapsible implant.

6. The system of claim 5, wherein the internal diameter of the inner tubular structure narrows radially for at least some portion, compressing the grasper upon entry of the inner tubular structure into the outer tubular structure, thereby causing the grasper to grasp and stabilize the catheter.

7. The system of claim 6, wherein the internal diameter of the inner tubular structure widens radially for at least some portion, allowing the grasper to expand upon further entry of the inner tubular structure into the outer tubular structure, thereby causing the grasper to release the catheter.

* * * * *